United States Patent [19]

Cutler et al.

[11] Patent Number: 4,609,584
[45] Date of Patent: Sep. 2, 1986

[54] ABSORPTIVE DEVICES

[75] Inventors: Larry P. Cutler, Eagan; Paul F. Guehler, White Bear Lake; Thomas I. Insley, Lake Elmo, all of Minn.

[73] Assignee: Minnesota Mining and Manufacturing Company, St. Paul, Minn.

[21] Appl. No.: 777,742

[22] Filed: Sep. 19, 1985

[51] Int. Cl.$^4$ .............................................. B32B 3/00
[52] U.S. Cl. .................................. 428/156; 428/284; 428/286; 428/913; 604/383
[58] Field of Search ............ 428/156, 284, 286, 315.5, 428/913; 604/383

[56] References Cited

U.S. PATENT DOCUMENTS 4,539,256  9/1985  Shipman ........................... 428/315.5

Primary Examiner—James J. Bell
Attorney, Agent, or Firm—Donald M. Sell; James A. Smith; Edward T. Okubo

[57] ABSTRACT

A microporous liquid impermeable but vapor permeable sheet material useful as a backsheet for disposable absorptive devices such as disposable diapers, incontinent devices, sanitary napkins, and panty liners is disclosed. This backsheet provides unexpected useful attributes such as compatibility with available closure tapes and embossibility with translucent patterns.

6 Claims, 3 Drawing Figures

ABSORPTIVE DEVICES

FIELD OF INVENTION

The present invention relates generally to disposable absorptive devices such as disposable diapers, incontinent devices, sanitary napkins, and panty liners. In particular, this invention relates to backsheets for these absorptive products which are impermeable to body liquids but permeable to evaporated body fluids.

BACKGROUND OF THE INVENTION

Disposable absorptive devices are well known. Numerous disposable products in the form of diapers, incontinent devices, sanitary napkins, and panty liners are readily available to the consumer. The function of all of these devices is to absorb and retain body fluids. The backsheet used to cover these products is typically a flexible plastic film which is impermeable to liquids and vapors. The function of the backsheet is to contain body fluids within the absorbent material and to prevent liquid passage which could cause soiling of garments worn by the user or other surroundings such as bedding. A major drawback of the conventional liquid impermeable backsheet is that it is also vapor impermeable. The disadvantage of a vapor impermeable backsheet is that body fluids in the absorptive device are unable to evaporate thus creating a hot saturated absorbent mass. Since this hot saturated absorbent mass is held against the user's body, an unpleasant and uncomfortable feeling to the user is unavoidable. It is also believed that rashes and irritations are more likely among users of disposable absorptive devices which incorporate a vapor impermeable backsheet.

Prior workers have attempted various methods to facilitate removal of vapors in disposable absorptive devices. U.S. Pat. No. 3,989,867 discloses an absorptive device having a backsheet with bosses and small apertures at the apex of the bosses. The apertures are uniformly distributed and take up ½% to 10% of the available permeation area of the backsheet to allow vapor transmission while preventing liquid passage at typical pressures encountered in use. U.S. Pat. No. 4,059,114 relates to a disposable shield for garment protection and everyday feminine hygiene with a fluid barrier in the form of a soft, pliable, rattle-free, moisture vapor permeable layer which is preferably a liquid-impermeable layer of a blown microfiber web. European Patent Application No. 83305609.0 relates to a breathable panty liner with one or more plies of a fibrous, liquid repellent, air permeable layer. Said layer is comprised of treated cellulosic fibers or synthetic polymeric fibers of polyethylene, polypropylene, or polyester. None of these prior art devices utilize a microporous film to impart vapor-transmissive characteristics to the disposable absorptive device.

Microporous films or membranes have a structure that enables vapors to pass through them. The effective pore size is at least several times the mean free path of the flowing molecules, namely from several micrometers down to about 100 Angstroms. Such sheets are generally opaque, even when made of a transparent material, because the surfaces and the internal structure scatter visible light.

Microporous membranes or films have been utilized in a wide variety of applications such as for the filtration of solids, diffusion barriers or separators in electrochemical cells, and in cloth laminates for use as raincoats and other outer wear. Microporous membranes or films are also utilized to make surgical dressings, bandages, and in other fluid transmissive medical applications.

The art of preparing microporous films or membranes is not restricted but rather is replete with a wide variety of methods for producing such articles.

U.K. Patent Application GB No. 2,026,381 A discloses the preparation of membranes having a porous surface by blending polymer with a liquid component to form a binary two-phase system which, in the liquid aggregate state, has a region of miscibility and a region with miscibility gaps, forming a sheet of the blend, casting the film into a bath of the liquid component and removing the liquid component to provide porosity. The resultant non-oriented porous sheet has a relatively low tensile strength.

U.S. Pat. Nos. 3,953,566, 3,962,153, 4,096,227, 4,110,392, 4,187,390 and 4,194,041, describe the preparation of porous articles, including microporous sheets, formed exclusively of polytetrafluoroethylene (PTFE), a non-thermoplastic polymer, which are characterized by having polymer nodes connected by fibrils. Such articles are produced by extruding a paste comprised of PTFE particles and a lubricant, removing the lubricant and stretching and annealing the resultant product. The resultant product is a sintered, oriented porous film of PTFE.

U.S. Pat. Nos. 4,100,238 and 4,197,148 describe the preparation of microporous films by extruding a two component blend, solvent leaching one dispersed component and stretching the resultant leached film to obtain a desired porosity. The blend consists of polymer and a leachable, non-miscible substance. Once the leachable dispersed polymer phase is removed and the film oriented, a porous film results.

U.S. Pat. No. 3,679,540 discloses a method for making a microporous polymer film by cold stretching an elastic polymer film until porous surface regions are formed by film failure, hot stretching the cold stretched film until fibrils and pores or open cells are formed and then heat setting the resultant film. Controlled porosity is generally not attained in such films because they do not always uniformly fibrillate to a specific pore size.

Certain U.S. patents disclose the preparation of porous polymer films by blending into the polymer non-miscible leachable particulate substance such as starch, salts, etc., forming a sheet and leaching the particulate substance from the polymer sheet. Such U.S. Patents include U.S. Pat. Nos. 3,214,501 and 3,640,829. U.S. Pat. No. 3,870,593 discloses the preparation of a microporous polymer sheet by blending non-miscible, non-leachable filler into the polymer, forming a sheet of the blend and stretching the sheet to form pores which are initiated at the sites of the filler particles.

U.S. Pat. No. 4,539,256, which patent is hereby incorporated by reference, teaches a method of making a microporous sheet which comprises the steps of melt blending a crystallizable thermoplastic polymer with a compound which is miscible with the thermoplastic polymer at the polymer melting temperature but immiscible on cooling below the polymer melting temperature, forming a sheet of the melt blend, cooling the sheet to a temperature at which the compound becomes immiscible with the polymer to cause phase separation between the thermoplastic polymer and the compound to provide a sheet comprising a first phase comprised of particles of thermoplastic polymer in a second phase of said compound, orienting the film in at least one direction to provide a network of interconnected micropores throughout the sheet. The microporous sheet comprises about 30 to 80 parts by weight crystallizable thermoplastic polymer and correspondingly about 70 to 20 parts by weight of the compound. The oriented sheet has a microporous structure characterized by a multiplicity of spaced randomly dispersed, equiaxed, non-uniform shaped, non-porous particles of the thermoplastic polymer which are coated with the compound. Adjacent thermoplastic particles within the sheet are connected to each other by a plurality of fibrils consisting of the thermoplastic polymer. The fibrils radiate in three dimensions from each particle. The compound may be removed from the sheet, e.g., by solvent extraction.

The use of porous films as backsheets for disposable diapers is, of course, known. U.S. Pat. No. 4,347,844 relates to the preparation of a porous sheet by blending into the polymer a particulate substance, forming the sheet, breaking the particles within the sheet under a compressive force, and utilizing said sheet as a backsheet for a disposable diaper. U.S. Pat. No. 4,364,985 relates to the preparation of a porous sheet by blending into the polymer a particulate substance, forming a sheet, abrading or buffing the surface of the sheet, and using the resulting sheet as a backsheet for a disposable diaper. A disadvantage of these two porous backsheets is their relatively poor compatibility with commercially available closure tapes due to their poor physical strength.

Another problem with known microporous backsheets is their lack of user identification as a vapor permeable backsheet. Since microporous film is generally opaque white due to light scattering in the internal structure, microporous backsheets appear identical to the conventional vapor impermeable plastic backsheets.

SUMMARY OF THE INVENTION

The present invention provides a microporous backsheet for disposable absorptive devices such as disposable diapers, incontinent devices, sanitary napkins, and panty liners which is impermeable to liquid body fluids but permeable to evaporated body fluids, compatible with various closure tapes or hot melt adhesives, and can be provided with a means for user perception of breathability. A backsheet with these characteristics simultaneously provides a barrier to liquid passage which is essential in all absorptive devices to prevent soiling of garments and surroundings, a means for vapor transmission allowing for evaporation of absorbed liquids resulting in a drier, cooler absorptive device, a means for closure and reclosure with available tapes or application of hot melt adhesives for garment attachment, and a means for embossing translucent patterns and logos providing a distinction from conventional vapor impermeable backsheets and a perception of breathability to the consumer.

DETAILED DESCRIPTION OF THE INVENTION

Figure 1:
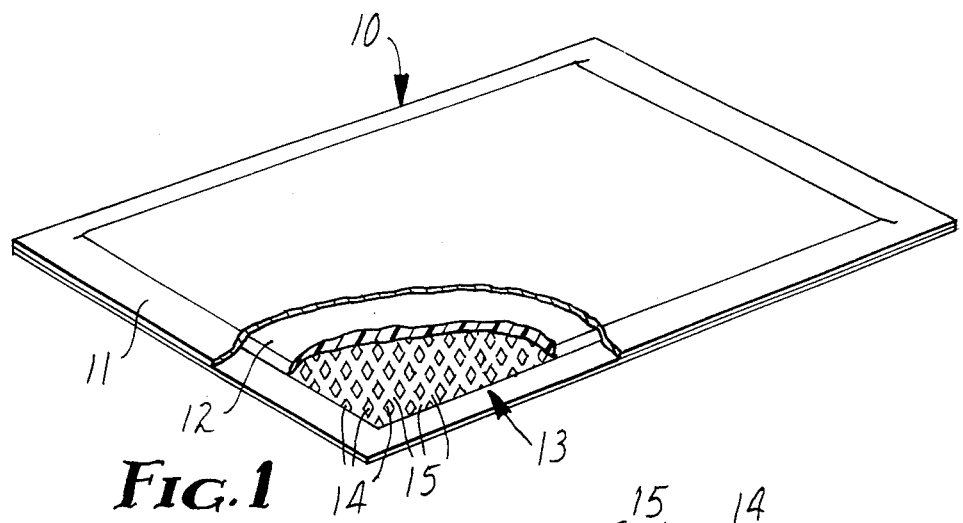
FIG. 1 is a perspective view, partially cut away, of a disposable diaper of the present invention.

Referring to the drawings, an exemplary disposable absorptive device of this invention in the form of a disposable diaper 10 is illustrated in FIG. 1. Diaper 10, as shown, comprises a surface sheet 11, an absorbent pad 12 and a backsheet 13. Since diaper 10 and each of the disposable absorptive devices of the present invention are, except for the liquid impermeable, vapor permeable backsheet, all of otherwise conventional construction, their specific constructional features will not be further described herein. The backsheet can be an unembossed sheet or may be embossed with a translucent pattern as shown for reasons to be hereinafter described.

Backsheet 13 or 20 (which are freely interchangeable) is prepared according to U.S. Pat. No. 4,539,256 using polyethylene as the polymer and mineral oil as the compound additive. Said sheet, due to its microporous structure, provides sufficient liquid holdout and vapor transmission for use as the backsheet in disposable absorptive devices.

It is believed to be desirable to provide to the user a means to readily identify a disposable absorptive device as being "breathable". A translucent pattern on the microporous backsheet 13 or 20 would provide such an indicia of "breathability" since the translucent regions would appear as apertures or discontinuities in the opaque white backsheet. The backsheets 13 or 20 of the present invention can be embossed to provide such a translucent pattern.

Prototype units of absorptive devices were prepared using conventional commercially available products except for substitution of the conventional backsheets with samples of the aforementioned polyethylene microporous backsheets of the present invention. Substantial water loss resulting from transmission of vapors through the backsheet was observed as well as a noticeable cooling of the device due to latent heat loss from the evaporated fluids.

Preparation of microporous sheets according to U.S. Pat. No. 4,539,256 is divided into four steps: (a) melt blending a crystallizable thermoplastic polymer such as polyethylene with a compound additive such as mineral oil; (b) forming a sheet of the melt blended solution; (c) cooling the sheet to achieve phase separation of the two components; and (d) orienting the sheet in at least one direction. The compound additive may be removed from the sheet by various means including solvent extraction. In the case of the microporous film prepared with polyethylene and mineral oil, the solvent 1,1,1-trichloroethane can be used for the extraction of the mineral oil from the microporous polyethylene sheet. It was found that the amount of mineral oil removed from the microporous polyethylene sheet could be controlled by varying the time the sheet was in contact with the solvent. In addition, it was found that the amount of mineral oil left in the sheet, termed as residual oil, had a direct effect on the physical properties on the microporous sheet.

In the application of this microporous sheet as a backsheet for sanitary napkins and panty liners, it is necessary for the backsheet to be compatible with hot melt adhesives typically coated on the backsheet for attachment to the user's undergarments. It was unexpected that a sheet containing even a trace amount of residual oil would be compatible with hot melt adhesives. Surprisingly, it was found that hot melt adhesives could be applied to microporous sheets containing considerable amounts of residual mineral oil with little or no effect on anchorage.

When the microporous sheet is used as a backsheet for disposable diapers and incontinent devices, it is necessary that the sheet be compatible with known tape closure systems. It was unexpected that a sheet containing any residual oil would be compatible with commonly used closure tapes. Again the contrary was found—commercially available closure tapes could be applied to sheets containing substantial amounts of residual mineral oil and still provide sufficient bond security, be readily removed and reapplied. It was also found that the adhesion level of the closure tape to the microporous backsheet could be adjusted by the amount of residual mineral oil in the sheet. This provides an option for obtaining different levels of adhesion without changing the tape closure system. This method of producing backsheets with an acceptable adhesion level is a further unexpected part of the present invention.

Of course, it would not be advantageous to adjust adhesion level by altering the residual mineral oil level if other key properties such as vapor transmission and water holdout would be adversely affected. Moisture vapor transmission rates, determined using the method described in ASTM E 96-80 and commonly known as MVTs, were found not to be adversely affected by residual mineral oil up to about 30 weight percent in the sheet. MVTs of a sheet with about 30 weight percent residual oil were at an adequate level to permit use of the sheet as a backsheet for disposable absorptive devices. An MVT of 1200 grams per square meter per 24 hours measured at 90° F. and 50% relative humidity would be sufficient for a backsheet of an absorptive device. Water holdout properties were not adversely affected by the residual mineral oil. Using a hydrostatic pressure unit, water holdout values were measured. Sheets with about 30 weight percent residual mineral oil did not allow any liquid passage at pressures up to 1.8 psi. This pressure is well above the typical pressures encountered in usage of disposable absorptive devices.

As earlier noted, consumers of disposable absorptive products would most likely associate a translucent patterned sheet with "breathability". To obtain a translucent pattern on the microporous polyethylene backsheets, an embossing step was used after the sheets had been formed. Embossing can be performed either thermally or mechanically. Microporous sheets appear opaque due to light scattering in their internal structure even when prepared with originally transparent material. Embossing is believed to collapse the impressed area of the microporous sheet structure thus transforming the opaque areas into translucent regions. The translucent regions could be designed into a geometric pattern or even a product logo. Surprisingly, translucent regions up to 50% of the total surface area do not appear to adversely affect the vapor transmissive properties of the sheets.

The following Examples are provided to illustrate the invention but are not intended to be limiting thereof.

EXAMPLE 1

A microporous sheet was prepared using the method described in U.S. Pat. No. 4,539,256 with a composition of 55.8 weight percent mineral oil and 44.2 weight percent high density polyethylene designated GM-9255 available from American Hoechst (Somerville, NJ) was used. The mineral oil was removed to provide varying levels of residual mineral oil using 1,1,1-trichloroethane for extraction in a seven tank solvent washing unit. Residual mineral oil weight percentages of 7.1 to 23.5% were obtained. Films were machine direction oriented 275% and then oriented 275% in the transverse direction. Samples were tested for tape adhesion using two methods: (1) a one inch wide matte finished polypropylene backed tape with an SIS block copolymer synthetic rubber based adhesive (Tape XMF-9.31.34 3M Company, St. Paul, MN) was rolled down on the sheet with a mechanical 100 gram roller and then peeled away at 90 degrees at a rate of 12 inches per minute in an Instron testing unit. The peel force was recorded as adhesion in grams per inch of width. (2) Procedure (1) was repeated using a 4.5 pound (2043 gram) roller and the force again recorded as grams per inch of width. Vapor transmission was measured at 90° F. and 30% relative humidity in a circulating air oven using ASTM method E 96-80. Data collected is shown in Table I.

TABLE I

| WEIGHT % RESIDUAL OIL | METHOD (1) ADHESION (grams/inch) | METHOD (2) ADHESION (grams/inch) | MVT @ 90° F./ 30% R.H. (grams/m²/24 hrs.) |
|---|---|---|---|
| 7.1 | 814 | 1067 | 2883 |
| 8.3 | 863 | 1217 | 3306 |
| 11.7 | 782 | 1079 | 3156 |
| 13.7 | 764 | 799 | 3390 |
| 16.8 | 683 | 824 | 2826 |
| 18.1 | 674 | 930 | 2865 |
| 20.6 | 734 | 582 | 2755 |
| 23.5 | 596 | 579 | 2767 |

EXAMPLE 2

A microporous polyethylene sheet was prepared as in Example 1 with a composition of 60 weight percent mineral oil and 40 weight percent high density polyethylene. The sheets were washed with 1,1,1-trichloroethane and residual mineral oil weight percentages from 8.1% to 26.0% were obtained. The sheets were oriented 275% in the machine-direction and 275% in the transverse direction. The sheets were tested as described in Example 1 and results are given in Table II.

TABLE II

| WEIGHT % RESIDUAL OIL | METHOD (1) ADHESION (grams/inch) | METHOD (2) ADHESION (grams/inch) | MVT @ 90° F./ 30% R.H. (grams/m²/24 hrs.) |
|---|---|---|---|
| 8.1 | 822 | 1229 | 2753 |
| 11.6 | 848 | 938 | 2950 |
| 15.5 | 781 | 826 | 2863 |
| 19.2 | 699 | 694 | 3046 |
| 25.2 | 756 | 733 | 2749 |
| 26.0 | 633 | 664 | 2662 |

It should be noted that the tape adhesion values reported in Tables I and II are specific values for sheets of the present invention with varying levels of residual oil and the specific synthetic rubber based adhesive tape used. Experience has shown that backsheets exhibiting tape adhesion values as low as 400 grams per inch width and as high as 1200 grams per inch width are useful.

EXAMPLE 3

A sample of microporous film backsheet was obtained from a disposable diaper available from the KAO Soap Company of Japan. Said microporous film backsheet is believed to be a blend of thermoplastic polymer and a particulate filler (calcium carbonate). This sample was tested as described in Example 1.

| SAMPLE | METHOD (1) ADHESION (grams/inch) | METHOD (2) ADHESION (grams/inch) | MVT @ 90° F./ 30% R.H. (grams/m²/24 hrs.) |
|---|---|---|---|
| KAO | 732* | 952 | 2651 |

*Film sample stretched and distorted during tape peel

EXAMPLE 4

The moisture vapor transmission test method as described in ASTM E 96-80 was modified to simulate usage in a disposable absorptive device. Instead of using water in the test dish, the test dish was filled with an absorbent material such as celluosic fluff and saturated with water. The sample was sealed over the absorbent mass and the test was then run per the ASTM method.

A sample of microporous film prepared as in Example 1, washed with 1,1,1-trichoroethane to 0.8 weight percent residual oil, and oriented 250% in the machine-direction and 250% in the transverse direction was tested using this modified MVT method.

Various absorbent materials were used in the test including wood pulp, absorbent tissue (Fort Howard Paper Co., No. 865 pulp nonwoven), a polypropylene blown microfiber (BMF) web loaded with a particulate superabsorbent (J-500 from Grain Processing Co., Muscatine, IA), a proprietary nonwoven polyethylene terephthalate web bonded by a polyacrylate supersorbent and a BMF web mixture with a superabsorbent fiber (Lanseal, Japan Exlan Ltd., Osaka, Japan). Test results are given in Table III.

TABLE III

| Absorbent Material | Amount Used | Water Added | Modified MVT 100° F./22% R.H. (grams/m²/24 hrs.) |
|---|---|---|---|
| Wood Pulp | 2.07 grams | 50 ml | 13,945 |
| Absorbent Nonwoven | 3.34 grams | 50 ml | 11,256 |
| BMF/Superabsorbent | 3.05 grams | 50 ml | 10,242 |
| Superabsorbent-bonded nonwoven | 0.72 grams | 50 ml | 11,719 |
| BMF/Lanseal fiber | 1.56 grams | 50 ml | 11,235 |

EXAMPLE 5

Figure 2:
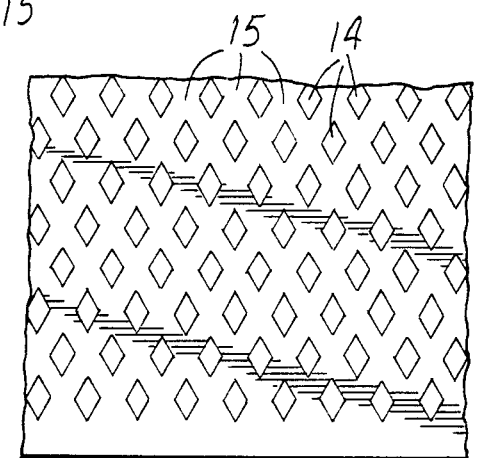
FIG. 2 is an enlarged plan view of a portion of the backsheet of the diaper of FIG. 1.
Figure 3:
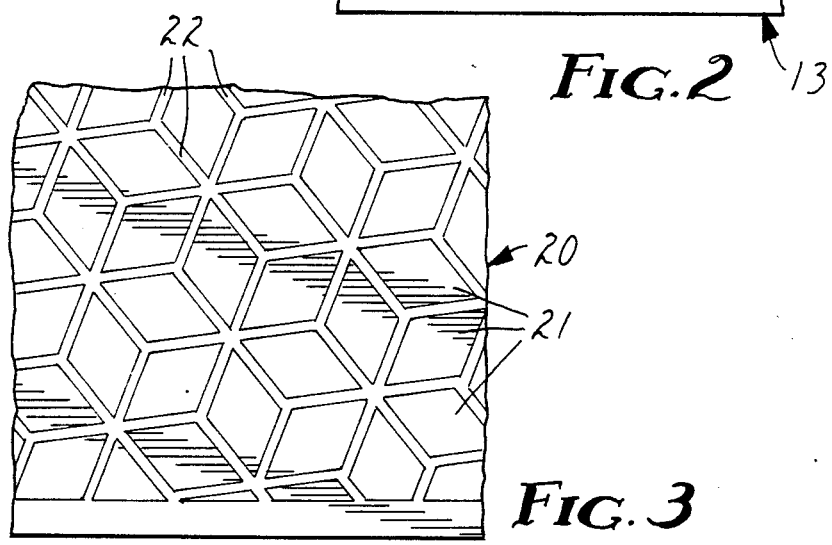
FIG. 3 is an enlarged plan view of a portion of another backsheet.

A microporous sheet prepared as described in Example 1 was embossed with various patterns using different methods:

(1) The sheet was placed on a metal mesh screen and rolled with a 30 pound steel roller. A pattern of translucent dots was obtained.
(2) The sheet 13 was run through a nip using a heated floating calendar roll and an engraved embossing roll with a diamond pattern. A roll pressure of 25 pounds and roll temperature of 150° F. was used resulting in a pattern of translucent diamonds 14 and opaque interconnecting web portion 15 shown in FIG. 2.
(3) The screen used in (1) was replaced with a diamond patterned screen, and the same roller was used to produce sheet 20 with the translucent pattern shown in FIG. 3 comprised of opaque diamonds 21 and interconnected translucent web portion 22.
(4) The embossing roll from (2) was replaced with an embossing roll with a hexagonal pattern. The same conditions were used to produce a pattern of translucent hexagons.

Samples of the embossed sheets were tested for moisture vapor transmission using the modified method described in Example 4 with the results shown in Table IV.

TABLE IV

| Embossed Pattern | Modified MVT @ 100° F./22% R.H. (grams/m²/24 hrs.) |
|---|---|
| (1) Dot | 10,738 |
| (2) Translucent Diamonds | 12,290 |
| (3) Opaque Diamonds | 11,690 |
| (4) Hexagonal | 10,572 |
| Control (non-embossed sample) | 11,462 |

EXAMPLE 6

A microporous polyethylene backsheet as described in Example 4 was substituted into a Stayfree Silhouette Maxi-Pad device produced by the Personal Products Company in place of its conventional backsheet. The thus modified Maxi-Pad device was saturated with 70 ml of deionized water and the body facing side was sealed with a vapor impermeable tape to prevent vapor transmission through the body facing side. The modified Maxi-Pad device was weighed and placed in a 90° F. oven for one hour along with a conventional Stayfree Silhouette Maxi-Pad device which had also been saturated with 70 ml of water and sealed with vapor impermeable tape on the body facing side. When the devices were removed, the modified Maxi-Pad device felt perceivably cooler than the conventional device which was still hot and saturated. The modified Maxi-Pad device lost 6.5 grams of water in the one hour period while the conventional Maxi-Pad device lost only 0.6 grams in the one hour period.

EXAMPLE 7

An Always panty liner produced by Procter and Gamble Company was modified by substituting its barrier layer (a vapor impermeable plastic sheet) with a layer of the microporous backsheet of Example 4 as in Example 6. This modified liner was tested side by side with a conventional Always panty liner. The panty liners were wetted with 50 ml of water, sealed on the body facing side, and placed in a 90° F. circulating air oven. The device modified with a microporous backsheet lost 1.8 grams in the one hour period and the conventional device lost 1.0 grams in the same one hour period.

EXAMPLE 8

A conventional disposable diaper with a wing-fold design was modified with a microporous backsheet using the procedure described generally in Examples 6 and 7. Some diapers were wetted with 250 ml of water and some diapers were wetted with 500 ml of water. The diapers were placed in a 100° F. circulating air oven and weight loss was monitored. Results are shown in Table V.

TABLE V

| DIAPER CONSTRUCTION | AMOUNT WATER ADDED | WEIGHT LOSS PER HOUR @ 100 F. |
|---|---|---|
| Conventional | 250 ml | 0.5 grams/hr |
| Modified | 250 ml | 13.6 grams/hr |

TABLE V-continued

| DIAPER CONSTRUCTION | AMOUNT WATER ADDED | WEIGHT LOSS PER HOUR @ 100 F. |
| --- | --- | --- |
| Conventional | 500 ml | 0.9 grams/hr |
| Modified | 500 ml | 16.2 grams/hr |

What is claimed is:

1. A microporous liquid impermeable but vapor permeable sheet material useful as the backsheet in a disposable absorptive device comprising about 30 to 80 parts by weight of a crystallizable thermoplastic polyethylene polymer and about 70 to 20 parts by weight of a hydrocarbon compound with which said thermoplastic polymer is miscible and in which said thermoplastic polymer will dissolve at the melting temperature of said thermoplastic polymer but will phase separate on cooling to a temperature at or below the crystallization temperature of said thermoplastic polymer, said microporous sheet material having an internal structure characterized by a multiplicity of spaced, randomly dispersed, non-uniform shaped, equiaxed particles of said thermplastic polymer coated with up to about 30 weight percent of said hydrocarbon compound, adjacent coated particles throughout said material being separated from one another to provide said material with a network of interconnected micropores and said adjacent thermoplastic polymer particles being connected to each other by a plurality of fibrils consisting of said thermoplastic polymer, said microporous sheet material having an embossed pattern thereon which covers up to 50% of the surface area of the film thereof.

2. Sheet material according to claim 1 having a moisture vapor transmission rate of at least 1200 grams per square meter per 24 hours at 90° F. and 50% relative humidity.

3. Sheet material according to claim 1 having an adhesion value to a synthetic rubber based adhesive in the range of about 400 grams per inch width and 1200 grams per inch width.

4. A disposable absorptive device including as a component thereof a microporous sheet material according to claim 1.

5. A disposable absorptive device including as a component thereof a microporous sheet material according to claim 2.

6. A disposable absorptive device including as a component thereof a microporous sheet material according to claim 3.

* * * * *